US007014862B2

(12) United States Patent
Myatt et al.

(10) Patent No.: US 7,014,862 B2
(45) Date of Patent: Mar. 21, 2006

(54) CHEWABLE COMPOSITIONS CONTAINING A GEL-FORMING EXTRACT OF PSYLLIUM

(75) Inventors: Graham John Myatt, Bracknell (GB); Christopher Neil Harrison, Langstone Hampshire (GB); Paul Alfred Cimiluca, Cincinnati, OH (US); Theresa Marie Kajs, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/368,225

(22) Filed: Feb. 18, 2003

(65) Prior Publication Data

US 2003/0215501 A1    Nov. 20, 2003

Related U.S. Application Data

(60) Provisional application No. 60/381,848, filed on May 20, 2002.

(51) Int. Cl.
*A61K 9/20* (2006.01)
*A61K 9/28* (2006.01)
*A61K 9/48* (2006.01)
*A61K 47/00* (2006.01)

(52) U.S. Cl. .................. 424/441; 424/439; 424/464; 424/466; 424/474

(58) Field of Classification Search ............. 424/464, 424/474, 479, 480, 489, 490, 491, 493, 494, 424/439, 441, 466
See application file for complete search history.

(56) References Cited

U.S. PATENT DOCUMENTS

| 4,999,200 | A | * | 3/1991 | Casillan .................. 424/480 |
| 5,356,618 | A | | 10/1994 | Daggy et al. |
| 5,425,945 | A | | 6/1995 | Barbera |
| 5,466,469 | A | * | 11/1995 | Kuhrts .................... 424/451 |
| 5,651,988 | A | | 7/1997 | Olinger et al. |
| 6,251,421 | B1 | * | 6/2001 | Niazi ....................... 424/441 |
| 6,287,609 | B1 | | 9/2001 | Marlett et al. |
| 2003/0180400 | A1 | * | 9/2003 | Nakamura et al. ........ 424/738 |

FOREIGN PATENT DOCUMENTS

WO    WO 93/08814 A1  *  5/1993
WO    WO 00/74689 A1  *  12/2000

OTHER PUBLICATIONS

Marteau P et al: "Digestibility And Bulking Effect Of Ispaghula Husks In Healthy Humans", GUT, British Medical Association, London, GB, vol. 35, 1994, pp. 1747-1752, XP002092236 Issn: 0017-5749 table 1.

Orr, William C et al: "A Comparison Of Dietary Fiber Supplements In The Treatment Of Mild Constipation", American Journal Of Gastroenterology, vol. 95, No. 9, Sep. 2000, pp. 2545-2546, XP009015866.

* cited by examiner

*Primary Examiner*—Thurman K. Page
*Assistant Examiner*—S. Tran
(74) *Attorney, Agent, or Firm*—Karen F. Clark; Kelly L. McDow-Dunham; Kristin Kohler

(57) ABSTRACT

Oral compositions, suitable for chewing, comprising a gel-forming polysaccharide isolated from psyllium seed husks and an excipient that is fast dissolving in the oral cavity, provide good aesthetics and acceptable mouthfeel as perceived by the consumer. The oral compositions are useful for normalizing bowel function, reducing human serum cholesterol levels and treatment of other gastrointestinal disorders.

37 Claims, No Drawings

CHEWABLE COMPOSITIONS CONTAINING A GEL-FORMING EXTRACT OF PSYLLIUM

CROSS REFERENCE TO PRIORITY APPLICATION

This application claims priority under Title 35, United States Code 119(e) from Provisional Application Ser. No. 60/381,848, filed May 20, 2002.

FIELD OF THE INVENTION

The present invention relates to oral compositions useful for treatment of gastrointestinal disorders. In particular, the present invention relates to oral compositions comprising a gel-forming polysaccharide isolated from psyllium seed husks, which have good aesthetics and acceptable mouthfeel as perceived by the consumer. The oral compositions are useful for normalizing bowel function, reducing human serum cholesterol levels, and treatment of other gastrointestinal disorders.

BACKGROUND OF THE INVENTION

Psyllium seed husk containing products are currently widely used for normalizing bowel function and Taxation. It has also been shown that psyllium seed husk is effective for reducing human serum cholesterol levels and in controlling blood glucose levels in diabetics.

These benefits are typically achieved by ingestion of psyllium seed husk, which is obtained from the seed coat from plants of the Plantago genus. To render a laxative effect, a typical human dose of psyllium seed husk is from about 3 grams to about 20 grams, taken from about 1 to about 3 times per day. In order to administer such a large amount of psyllium seed husk, the husk is often milled or ground and subsequently dispersed in water or an aqueous beverage for consumption by the user (for example, META-MUCIL®, sold by The Procter & Gamble Company). In addition to milling, typically, sanitization of the psyllium seed husk is performed prior to any further processing, in order to reduce microbial contamination of the psyllium seed husk. This sanitation step can be costly and difficult to perform.

Psyllium seed husk contains natural mucilage, forming a gelatinous mass on contact with water. Thus, milled psyllium seed husk, with its increased surface area, exhibits very poor disperability and mixability in water as the particles tend to agglomerate. Hydration takes place over the surface of the agglomerated aggregates to form gel-coated lumps, the interiors of which are still substantially dry. These lumps are extremely difficult to disperse. Various methods have been employed to improve the dispersability of milled psyllium husk in an aqueous medium. For example, U.S. Pat. No. 5,425,945 to Barbera, discloses a drink mix composition comprising agglomerated psyllium seed husk with an edible acid uniformly dispersed throughout the agglomerating coating to obtain improved mixability and dispersability.

However, once dispersed in an aqueous solution, the agglomerated psyllium husk quickly begins to hydrate and gel with an accompanying increase in the viscosity of the drink solution. Again, various methods have been employed to reduce this gelation rate and provide an aesthetically pleasing product. U.S. Pat. No. 5,356,618, to Daggy et al., teaches that the addition of calcium citrate malate to a composition comprising milled psyllium seed husk results in a reduced gelation rate of the husk when mixed with an aqueous solution. However, despite these improvements, the consumer of the psyllium seed husk suspension typically drinks the liquid in a relatively short period of time (less than about two minutes) in order to avoid having to drink an aesthetically unpleasant, high viscosity liquid.

Sanitized, milled psyllium seed husk has been incorporated in baked items, such as cookies, crackers and similar food items to render solid dosage forms. However, the fast gelation of the psyllium husk is noticeable in these preparations as well. Psyllium husk containing preparations have a tendency to begin to gel in the mouth during consumption, resulting in an unpleasant mouthfeel and poor aesthetics. It is generally necessary to consume such baked items with significant amounts of water or another beverage for ease of swallowing. In addition, such solid psyllium seed husk preparations must be large in size or, alternatively, multiple preparations must be consumed in order to deliver an effective amount of psyllium seed husk. Therefore, a psyllium containing composition that is convenient, easily administered and has acceptable aesthetics and good mouthfeel characteristics is still needed.

Previously the focus has been to provide a swallowable psyllium-containing tablet with acceptable dissolution properties, thus avoiding problems of poor mouthfeel. U.S. Pat. No. 4,999,200, to Casillan, teaches a swallowable psyllium-containing tablet comprising psyllium, a binder, a wetting agent and a disintegrating agent. Unfortunately, swallowable psyllium tablets, while convenient, often have poor dissolution properties. Like the powdered drink mix, once introduced into an aqueous environment hydration takes place over the surface of the pill, creating a gel coating, the interiors of the pill remain substantially dry. For swallowable pills this can lead to incomplete dissolution in the gastrointestinal tract. Therefore, there is a need to provide a psyllium-containing dosage form, suitable for chewing, where the chewing action disintegrates the tablet into smaller, discrete particles prior to swallowing but which undergoes minimal gelling in the mouth, and has acceptable mouthfeel and good aesthetics as perceived by the consumer.

Methods of fractionating psyllium seed husk into various polysaccharide components are known. These fractions of psyllium seed husk deliver the same therapeutic benefits as psyllium seed husk and can act as a suitable substitute for psyllium seed husk in various dosage forms. For example, U.S. Pat. No. 6,287,609 to Marlett et al., teaches a multiple extraction process for obtaining three distinct fractions from psyllium husk, including an alkali soluble/acid gel-forming fraction, an alkali insoluble fraction, and an acid soluble fraction. The alkali soluble/acid gel-forming fraction has a slower rate of gelation than non-fractionated psyllium seed husk.

It has been surprisingly discovered that the use of a gel-forming polysaccharide derived from psyllium seed husk, when combined with certain excipients that are fast dissolving in saliva, renders an oral composition that undergoes minimal gelling in the mouth of the consumer prior to swallowing and has good aesthetics.

It has also been discovered that combining a comparatively slow dissolving excipient at relatively low levels with the gel-forming polysaccharide and the fast dissolving excipient, results in an oral compositions with improved aesthetics and better mouthfeel as perceived by the consumer.

SUMMARY OF THE INVENTION

The present invention relates to oral compositions comprising from about 10% to about 90% of a gel-forming polysaccharide isolated from psyllium seed husk and from about 10% to about 90% of an excipient that is fast dissolving in the salivary conditions of the oral cavity. In particular the gel-forming fraction is a polysaccharide comprising primarily xylose and arabinose in a dry weight ratio at least about 3:1, xylose to arabinose. In one embodiment the fast dissolving excipient is a polyol selected from the group consisting of sorbitol, isomalt and mixtures thereof.

The present invention also relates to oral compositions comprising a gel-forming polysaccharide isolated from psyllium seed husk; a fast dissolving excipient, as described above; and low levels of a comparatively slow dissolving excipient. The slow dissolving excipient is present in an amount sufficient to modify the mouthfeel of the oral composition to render a chewable dosage form with acceptable aesthetics, perceived by the consumer as a creamy mouthfeel. In one embodiment the slow dissolving excipient is present at levels from about 0.01% to about 30%.

The oral composition may be in any solid oral dosage form. In one embodiment the compositions herein may be compressed into a chewable tablet. Unlike powdered psyllium seed husk, the gel-forming polysaccharide derived from psyllium is compressible, particularly where the gel-forming polysaccharide has been fluid bed dried to a powder form. Therefore, it is not necessary to add a binder to compositions of the present invention for tabletting purposes.

The oral compositions described herein are useful for normalizing bowel function, reducing human serum cholesterol levels, and treatment of other gastrointestinal disorders. In addition, the oral compositions of the present invention have reduced levels of allergenic protein as compared to psyllium seed husk containing compositions.

All documents cited are, in relevant part, incorporated herein by reference; the citation of any document is not to be construed as an admission that it is prior art with respect to the present invention.

DETAILED DESCRIPTION OF THE INVENTION

Definitions

By "safe and effective amount", as used herein, is meant an amount of an active agent (e.g. the gel-forming polysaccharide) high enough to significantly improve the condition to be treated, but low enough to avoid serious side effects (at a reasonable benefit/risk ratio), within the scope of sound medical judgment. The "safe and effective amount" may vary with the particular condition being treated, the age and physical condition of the patient being treated, the severity of the condition, the duration of treatment, the nature of concurrent therapy, the specific form of the source employed, and the particular vehicle from which the agent is applied.

The term "oral composition" as used herein means any pharmaceutical composition intended to be administered to the stomach of a mammal via the mouth of said mammal.

The term "solid oral dosage form" refers to a physically discrete unit suitable as a unitary dosage for human subjects and other mammals, each containing a predetermined quantity of active material (e.g. the gel-forming polysaccharide) calculated to produce the desired therapeutic effect. Solid oral dosage forms that are suitable for the present compositions include tablets, pills, capsules, lozenges, chewable tablets, troches, cachets, pellets and the like. In one embodiment the compositions of the present invention are in the form of chewable tablets containing particles or granules of the gel-forming polysaccharide.

For purposes herein, the term "raw" refers to psyllium seed husk that has not been sanitized (prior to the initial alkaline solubilization step), by any method known in the art, such as by steam sanitization.

The term "compressible" as used herein refers to granules or powders that are capable of undergoing compaction, reversible deformation and finally irreversible deformation as applied stress increases, ultimately resulting in a reduction in volume. Compressible powders or granules may be compressed into tablet form.

The term "direct compression" refers to the process of compressing tablets directly from powdered material. Direct compression is appropriate where the physical nature of the powdered material need not be modified prior to tabletting.

The term "swell volume" as used herein is the volume of gel mass formed when the gel-forming polysaccharide, equivalent to 0.5 grams psyllium on a weight basis (or 0.5 grams psyllium seed husk) are combined with water to a total volume of 100 mL (milliliters) in a cylinder at ambient temperature. The cylinder is inverted several times at the start of the test to insure thorough mixing, as well as at 4 hours and 8 hours from the start of the test. The swell volume is recorded 24 hours after the start of the test. Swell volume provides a measure of the ability of the gel-forming polysaccharide (or psyllium) to absorb water. The swell volume is reported in milliliters of swelled gel forming polysaccharide mass per grams of dry gel forming polysaccharide.

Percentages and ratios herein are by weight of total composition, unless otherwise indicated.

Gel-Forming Polysaccharide

The present compositions comprise from about 10% to about 90% of a gel-forming polysaccharide, in one embodiment from about 25% to about 75%, in another embodiment from about 40% to about 60%. The gel-forming polysaccharide is comprised primarily of xylose and arabinose. The gel-forming polysaccharide obtained by the method disclosed herein is comprised primarily of xylose and arabinose. In one embodiment, the gel-forming polysaccharide has at least about 50% xylose and arabinose by weight, in another embodiment at least about 75% xylose and arabinose, in yet another embodiment at least about 80% xylose and arabinose. In one embodiment, the xylose to arabinose dry weight ratio is at least about 3:1, in one embodiment from about 3:1 to about 4.5:1, in another embodiment from about 3:1 to about 4:1 and in yet another embodiment from about 3.3:1 to about 3.6:1. In one embodiment the gel-forming polysaccharide comprises from about 55% to about 70% of xylose and from about 15% to about 20% of arabinose. In addition, low levels of galactose and uronic acid are present in the gel-forming polysaccharide of the present invention. For example, the level of galactose is less than about 2%, in one embodiment from about 1% to about 2%. The level of uronic acid is generally less than 10%. In one embodiment the dry weight ratio of xylose to galactose is more than about 25:1, in another embodiment more than about 30:1 and in yet another embodiment more than about 35:1. In one embodiment the dry weight ratio of xylose to uronic acid is more than about 5:1, in one embodiment about 10:1 and in yet another embodiment about 15:1. Generally, the gel-forming fraction has the following sugar composition:

| Component | Amount present in gel-forming polysaccharide |
|---|---|
| Xylose | From about 55% to about 70% |
| Arabinose | From about 15% to about 20% |
| Rhamnose | From 0% to about 5% |
| Mannose | From 0% to about 0.5% |
| Galactose | From about 1% to about 2% |
| Glucose | From 0% to about 0.5% |
| Uronic Acid | From about 0.5% to about 50% |

In one embodiment, the gel-forming polysaccharide of the present invention is extracted from psyllium seed husk in the following manner:

Step 1. Suspending unmilled psyllium seed husk in a dilute alkaline aqueous solution containing a reducing agent.

Step 2. Where previously unsanitized psyllium is utilized, disinfecting the alkali soluble and alkali insoluble material by any means known in the art such as pasteurization, irradiation, electron beam or pulsed light.

Step 3. Removing the alkali insoluble material by any process known in the art, for example centrifugation, filtration, expression or settling.

Step 4. Acidifying the solution to a pH of about 4.5 to about 6.5 by the addition of acid, to yield an acid gel-forming material, i.e. the gel-forming polysaccharide.

Step 5. Dewatering the gel material by the addition of a desiccant with high shear mixing and then separating the gel material from the desiccant/water solution.

Step 6. Extruding the gel material into individual particles with an average particle size of greater than 250 microns.

Step 7. Fluidized bed drying the gel material rendering the compressible gel-forming polysaccharide in powder form.

The starting material employed in the fractionation of psyllium seed husk may or may not be milled or physically altered or refined, prior to the initial alkaline solubilization step. U.S. Pat. No. 6,287,609 to Marlett et al., teaches that it is necessary for the psyllium seed husk to be processed so that it is in small pieces, prior to alkaline solubilization, for ease of separation of the viscous polysaccharides from the insoluble fibers of the psyllium husk. However, clumping and agglomeration of the milled psyllium seed husk occurs when the milled husk is added to the alkaline mixture. It has been discovered that the use of unmilled psyllium seed husk as an initial starting material avoids clumping or agglomerating of the psyllium material during mixing with the alkaline solution, but does not hinder the effectiveness of the alkaline solubilization step. The use of unmilled psyllium as a starting material for the fractionation provides a gel-forming polysaccharide with increased swell volume. The swell volume of the gel-forming polysaccharide obtained by the present invention is greater than about 40 milliliters of gel per 0.5 grams dry gel-forming polysaccharide, in one embodiment greater than about 50 milliliters of gel per 0.5 grams dry gel-forming polysaccharide. The percent yield of the gel-forming polysaccharide of the present invention is at least about 75%, in one embodiment at least about 80%. The psyllium seed husk of the present invention may or may not be sanitized prior to processing. The psyllium seed husk may be sanitized or unsanitized prior to alkaline solubilization. Where raw (unsanitized) psyllium is used in the fractionation process, a disinfection step is incorporated in the fractionation process and may be carried out as described below.

Alkaline solubilization (Step 1) of psyllium seed husk is known. Typically, previous alkaline solubilization processes utilized concentrations of strong bases and lacked the presence of a reducing agent. Recognizing the harsh nature of this treatment and the partial degradation of polysaccharide chains in the gel-forming fraction, it has been shown that a gel-forming fraction of psyllium husk could be obtained, presumably in a form more suitable for further fractionation, if desired, using a much less concentrated alkaline solution and a suitable reducing agent, such as borohydride. Though up to about 4N alkaline solution can be utilized, the concentration of base in the alkaline solubilization is at least about 0.1N and not more than about 10N; in one embodiment at least about 0.1N and not more than about 0.5N; and in yet another embodiment at least about 0.1N and not more than about 0.3N. Any standard base can be used in the alkaline extraction, including, but not limited to, sodium hydroxide, potassium hydroxide, lithium hydroxide, ammonium hydroxide, and tetramethyl ammonium hydroxide. A suitable ratio of psyllium seed husks to alkaline solution is from about 0.1 gram seed husk to about 400 ml (milliliters) of alkaline solution to about 4 grams seed husk to about 400 ml alkaline solution. The alkaline solubilization should be carried out at a pH of from about 9 to about 12.

A chemical reducing agent, such as borohydride, should be added to the alkaline solubilization step to minimize base-catalyzed depolymerization. Borohydrides suitable for this step include, but are not limited to, lithium borohydride, potassium borohydride and sodium cyanoborohydride. In one embodiment the reducing agent is sodium borohydride. An effective concentration of a reducing agent is from about 50 mg/L (milligrams/liter) to about 10 g/L (grams/liter), in one embodiment from about 100 mg/L to about 4 g/L, in another embodiment from about 500 mg/L to about 2 g/L, and in yet another embodiment from about 800 mg/L to about 1.2 g/L.

The time of solubilization can be varied from about 15 minutes to about 24 hours, in one embodiment from about 30 minutes to about 180 minutes, for optimum efficiency. Likewise, the temperature at which the solubilization step is conducted can vary from about 5° C. to about 40° C. In one embodiment the time of solubilization is from about 60 minutes to about 120 minutes at ambient temperature. The alkaline solubilization may optionally be carried out in a nitrogen atmosphere to prevent oxidation from occurring.

The disinfecting step, Step 2, is required when the psyllium seed husk has not been sanitized prior to mixing with the alkaline solution. If the unmilled psyllium seed husk is sanitized by any method known in the art, such as steam sanitation, prior to the alkaline solubilization step, this disinfection step is not necessary. Disinfection refers to inactivating, destroying, eliminating, or inhibiting the growth of microorganisms. In one embodiment these microorganisms are disease-producing agents. Disinfection of the combined alkali soluble and alkali insoluble fractions may be conducted by any means known in the art. For example, pasteurization, irradiation, electron beam and pulsed light are all acceptable means of disinfecting the alkali soluble and alkali insoluble fraction mixture. In one embodiment, the mixture is pasteurized. Pasteurization entails heating the mixture to a moderate temperature for a period of time to disinfect, without changing, to any extent, the chemical composition of the mixture. Pasteurization may be carried out at a temperature of from about 90° C. to about 120° C. for a period of from about 30 seconds to about 120 seconds.

The alkali insoluble material is separated from the alkali soluble materials in Step 3 of the fractionation. This can be accomplished by any separation means known in the art that will not alter substantially the insoluble material, for example centrifugation. One skilled in the art will know how to alter the time and force of the centrifugation to adapt the separation to different centrifuge rotors, plant materials and alkaline solutions. Other methods to accomplish this separation are well known in the art and may be better suited for large-scale production of the gel-forming polysaccharide, such as settling, filtration, or expression. Optionally, the insoluble material can be further washed with the alkaline solution and re-separated in an effort to improve the yield of the alkaline soluble material.

In Step 4 of the instant process, the alkaline soluble materials are acidified to a pH of from about 4.5 to about 6.5, in one embodiment from about 5 to about 6, to yield an acid gel-forming material, i.e. the gel-forming polysaccharide. Suitable acids for acidification include, but are not limited to, acetic, hydrochloric, sulfuric, oxalic, trichloroacetic and trifluoroacetic acids. The duration and temperature of the acidification can vary. The acidification may suitably take place at ambient temperature for about 2 hours, though the time and temperature may vary.

Optionally, a second extraction may be appropriate at this stage of the fractionation process. Where desired, the acid soluble and acid gel-forming fractions may be separated, by any means known in the art, such as centrifugation, settling, straining and the like. Again an optional washing with water, buffer, or other suitable solvent may be employed to improve the efficiency of the separation. This second extraction may be employed to deliver a more purified gel-forming polysaccharide, but may also lead to degradation and loss of some of the gel-forming polysaccharide. It has been found that multiple extraction steps are not necessary to yield a suitable gel-forming polysaccharide with increased swell volume and a reduced in gelation rate.

Excess water is then removed from the acid gel-forming polysaccharide fraction in Step 5 of the fractionation process. Any method known in the art may be used to dewater the gel material. In one embodiment the gel material may be dewatered by desiccation with a solvent, such as ethanol, acetone, methanol or isopropyl alcohol. The addition of the solvent may occur with high shear mixing. The gel material is then separated from the solvent/water mixture by any method known in the art. For ease and simplicity of drying, the solids content of the gel material should be at least about 50%, in one embodiment the solids content is at least about 75%, in another embodiment the solids content of the gel material is about 80%.

The gel material may be dried in any manner known in the art, such as lyophilization, fluidized bed drying or vacuum tray drying. In one embodiment, fluidized bed drying of the gelatinous material is employed. The gel material is extruded to form small grain-like particles and placed into a fluidized bed dryer. The particle size of the gel-forming polysaccharide should be greater than 250 microns, in one embodiment from about 250 microns to about 1000 microns, and in another embodiment from about 350 to about 750 microns. The fluidized bed dryer may be equipped to provide a cyclonic airflow, which helps prevent the particles sticking together and allows the particles to fluidize. The extruded particles are suspended in the column of air until dried to at least about 85% solids content. During drying, the gel material should be maintained at a temperature of less than about 75° C. It is preferred that the solids content of the gel material is greater than about 20% prior to fluidized bed drying. If necessary, previously dried gel material may be added by mixing to the low solids content gel material, prior to fluidized bed drying, to increase the solids content to greater than about 20%. Not intending to be bound by theory, it is believed that the fluidized bed drying technique renders a gel-forming polysaccharide powder composition wherein the individual particles retain a honeycomb shape. The honeycomb shape is useful to facilitate compression of the gel-forming polysaccharide powder, particularly by direct compression means, into a solid dosage form.

Importantly, the gel-forming polysaccharide of the present invention has reduced allergenicity when compared to milled, sanitized psyllium seed husk. As used herein the term "allergenicity" is a measure of the amount of allergenic protein present in the gel-forming polysaccharide. Psyllium seed husk contains specific protein fractions, which are considered allergens. Allergenicity is determined by extracting proteins from a sample of material (e.g. the gel-forming polysaccharide or psyllium seed husk) and then determining the allergenicity of those proteins by known electrophoresis techniques, such as sodium dodecylsulfate polyacrylamide gel electrophoresis (SDS-PAGE), or immunoblotting. One skilled in the art can readily utilize these techniques to evaluate the reduction in allergenicity of a material versus a control (e.g. psyllium seed husk). For example, U.S. Pat. No. 5,248,502, to Ndife, teaches that immunoblotting is used to determine the extent of IgE antibody binding to specific psyllium proteins, providing a measure of the allergenicity of psyllium protein fractions. The gel-forming polysaccharide fraction of psyllium husk obtained by the process described herein has reduced allergenicity in comparison to milled sanitized psyllium seed husk (the control). A reduction in allergenicity of greater than about 90% versus the control, in one embodiment greater than about 95% versus the control, is achieved by fractionating psyllium seed husk by the process described herein. Thus, the level of allergenic protein present in the gel-forming polysaccharide is less than about 10% of the allergenic protein present in psyllium seed husk, in one embodiment less than about 5% of the allergenic protein present in psyllium seed husk. Not intending to be bound by theory, it is believed that the reduction in allergencity is due to several factors. Allergenic proteins are believed to be mainly present in the alkali insoluble fraction, which is removed in large part during Step 3 of the fractionation process. The subsequent dewatering of the remaining gel material with a solvent/dessicant may result in denaturing of the proteins remaining in the gel material thereby further reducing allergenicity.

Fast Dissolving Expicient

The present compositions comprise from about 10% to about 90% of a fast dissolving excipient, in one embodiment from about 30% to about 70%, in another embodiment from about 40% to about 60%.

As used herein the term "fast dissolving excipient" is meant to describe those excipients that dissolve quickly in the salivary conditions of the oral cavity. To determine the dissolution rate of various excipients the following method is used, which simulates the environment of the oral cavity:

1) 2.5 grams of excipient material is weighed and hand pressed into a tablet. The tablet is pressed to a desired tablet "crush" hardness of approximately 8000 grams. The tablet "crush" hardness is measured by calculating the force, in grams, needed to crush the tablet.

2) To determine the tablet dissolution in the salivary environment of the oral cavity, commercially available artificial saliva, such as sterile refined porcine gastric mucin, is used. Saliva Orthana, manufactured by A/S Orthana Keisk Fabrik, Kastrup, Denmark is a suitable artificial saliva.
3) In a beaker, 450 mL (milliliters) of the artificial saliva is heated to 32° C. and stirred at 300 rpm (revolutions per minute) with a magnetic stirrer. 40 mL of the preheated saliva is removed and placed in a 60 mL beaker and stirred at 400 rpm.
4) The excipient tablet is added to the artificial saliva. The time in seconds for the tablet to breakup from a tablet shape into pieces is recorded as the tablet breakdown time. The time in seconds that the tablet takes to dissolve completely into the solution is recorded as the dissolution time.

Fast dissolving excipients are those excipients with a dissolution time of about 200 seconds or less based on the above method, in one embodiment about 150 seconds or less. Dissolution times of excipients may vary based on both chemical and physical properties, such as particle size. Fast dissolving excipients include but are not limited to fast saliva dissolving polyols, specifically the fast saliva dissolving sugar alcohols, selected from the group consisting of sorbitol, isomalt and mixtures thereof. In one embodiment the fast dissolving excipient is sorbitol. The average particle size of the fast dissolving excipient is at least about 250 microns, in one embodiment from about 250 microns to about 1000 microns; in another embodiment the average particle size is about 350 microns to about 750 microns. For ease of tabletting and flowability, the average particle size of the fast dissolving excipients should target the particle size of the gel-forming polysaccharide.

Slow Dissolving Excipient

The present compositions may comprise from about 0.01% to about 30% of a slower dissolving excipient, in one embodiment from about 0.1% to about 25%, in another embodiment from about 1% to about 20%.

As used herein the term "slow dissolving excipient" is meant to describe those excipients dissolve slowly in saliva. That is, slow dissolving excipients are those excipients that dissolve in saliva, after more than about 200 seconds, as determined by the above described method, in one embodiment more than about 250 seconds. The slow dissolving excipients include, but are not limited to, the slow saliva dissolving polyols, specifically the slow saliva dissolving sugar alcohols, selected from the group consisting of mannitol, maltitol, maltodextrin, xylitol and mixtures thereof. In one embodiment the slow dissolving excipient is mannitol. The average particle size of the slow dissolving excipient is at least about 250 microns, in one embodiment from about 250 microns to about 1000 microns, in another embodiment the average particle size is about 350 microns to about 750 microns. For ease of tabletting and flowability, the average particle size of the slow dissolving excipients should target the particle size of the gel-forming polysaccharide and the fast dissolving excipient.

Optional Ingredients

Once dried the individual gel-forming polysaccharide particles may be coated. Coating of the polysaccharide particles may further improve the mouthfeel and aesthetics of the present compositions. The coating acts as a barrier to water and, thus, dampens the hygroscopic action of the polysaccharide when placed on the tongue of the consumer. Acceptable coating materials include, but are not limited to, carnuba wax, polyethylene glycol, hydroxypropyl methylcellulose, copolymers of poly(acrylate, methacrylate), polymethacrylate, ethylcellulose, water-soluble polymers derived from Indian corn or mixtures thereof. Alternatively, a coating may be applied to a solid oral dosage form containing the gel-forming polysaccharide or to both the individual gel-forming polysaccharide particles and the final solid dosage form. The coating may be applied to all or a part of the solid oral dosage form, such as only the large flat surfaces of a tablet.

The amount of coating deposited on the tablet, or on the individual particles of polysaccharide is typically in the range of from about 2% to about 5% by weight of the tablet or granule. The coating may further comprise a plasticizer such as polyethylene glycol or polypropylene glycol. The amount of plasticizer may be from about 15% to about 40% by weight of the coating material. Dyes, pigments, flavorants, and other optional ingredients may be added to the coating material.

A lubricating agent may be added to the compositions of the present invention. Suitable lubricants include, but are not limited to, talc, magnesium stearate, calcium stearate, stearic acid, hydrogenated vegetable oils, polyethylene glycol, sodium benzate, sodium chloride, leucine, sodium lauryl sulfate, and magnesium lauryl sulfate. Lubricants are generally present at a level of about less than about 5% by weight and in one embodiment less than about 1%.

The compositions described herein may optionally further comprise one or more flavorants. These flavoring agents can be chosen from synthetic flavoring liquids and/or oils derived from plants, leaves, flowers, fruits and so forth, and combinations thereof. Representative flavoring liquids include: vanillin, sage, marjoram, parsley oil, spearmint oil, cinnamon oil, oil of wintergreen (methylsalicylate), peppermint oils, clove oil, bay oil, anise oil, and eucalyptus oil. Also useful are artificial, natural or synthetic fruit flavors such as citrus oils, including lemon, orange, banana, grape, lime, apricot and grapefruit, and fruit essences, including apple, strawberry, cherry, orange, pineapple and so forth; bean and nut derived flavors such as coffee, cocoa, cola, peanut, almond; and spices such as cinnamon, nutmeg, ginger and the like, and so forth. Additionally, flavor adsorbed onto a hydrophilic matrix may be included, e.g. "spray-dried" flavors. Furthermore, encapsulated flavors may be included. In one embodiment the flavorant comprises citric acid. The amount of flavorant employed is normally a matter of preference subject to such factors as flavor type and strength of flavor desired. The flavorant may be incorporated into one or more of the following: the tablet; the coating of the tablet; or the coating of the individual particles of gel-forming polysaccharide, where such coatings are employed. Flavorants may be present in amounts up to about 4%, in one embodiment about 0.01% to about 3.0%, in another embodiment about 0.2% to about 2.5%, by weight of the total composition.

One or more pigments, dyes, colorants and their corresponding lakes may also be added to modify the appearance of the compositions herein to render the product more acceptable to the consumer. Appropriate levels are selected for the particular impact that is desirable to the consumer. The levels of pigments and colorants may be in the range of about 0.001% to about 20%, in one embodiment from about 0.01% to about 15% and in another embodiment from about 0.1% to about 10% by total weight of the composition. Suitable pigments and colorants include talc, mica, magnesium carbonate, calcium carbonate, magnesium silicate, aluminum magnesium silicate, silica, titanium dioxide, zinc oxide, red iron oxide, brown iron oxide, yellow iron oxide, black iron oxide, ferric ammonium ferrocyanide, bismuth oxychloride, manganese violet, ultramarine, nylon powder, polyethylene powder, methacrylate powder, polystyrene powder, silk powder, crystalline cellulose, starch, titanated mica, iron oxide titanated mica, bismuth oxychloride, FD&C Red 40, D&C Reds 3, 22, 28, 33 and 36, FD&C Yellows 5 and 6, D&C Yellow 10, FD&C Blues 1 and 2, FD&C Green 3, beta-carotene, caramel, cochineal extract, canthaxanthinin, and mixtures thereof. Generally the particle size of the colorants, dyes, lakes and pigments included within the compositions of the present invention are about less about 250 microns and in one embodiment less than about 150 microns. To ensure uniform mixing and to prevent color separation in the resulting formulation, the colorant, dye, pigment or lake may be mixed with the gel-forming polysaccharide prior to the addition of other ingredients. Alternatively, the colorant, dye, pigment or lake may be incorporated into the coating of the tablet or the individual particles of gel-forming polysaccharide where such coatings are present.

One or more nutrients may be included in the compositions of the present invention. Nutrients include minerals, vitamins, oral nutritional supplements, enteral nutritional supplements, herbals and mixtures thereof. Useful minerals include calcium, phosphorus, zinc, manganese, potassium, sodium, chromium, cobalt, copper, fluorine, chlorine or chloride, iodine, iron, magnesium, molybdenum, selenium, silicon, boron, tin, vanadium and mixtures thereof. Vitamins can be included with minerals or used independently. Suitable vitamins include Vitamins A, C, B-6, B-12, B-13, D, E and K, thiamine, riboflavin, pantothenic acid, niacin, folic acid, nicotinamide, para-aminobenzoic acid, bioflavonoids, caranitine, coenzyme Q, laetrile, lipoic acid, biotin, pangamic acid, beta carotene, and mixtures thereof. Oral nutritional supplements include amino acids, lipotropics, fish oil, and mixtures thereof. Amino acids include, but are not limited to L-Tryptophan, L-Lysine, Methionine, Threonine, Levocarnitine or L-carnitine and mixtures thereof. Lipotropics include, but are not limited to, choline, inositol, betaine, linoleic acid, linolenic acid, and mixtures thereof. Fish oil contains large amounts of Omega-3 (N-3) polyunsaturated fatty acids, eicosapentaenoic acid and docosahexaenoic acid. Enteral nutritional supplements include, but are not limited to, protein products, glucose polymers, corn oil, safflower oil, medium chain triglycerides. Minerals, vitamins, oral nutritional supplements and enteral nutritional supplements are described in more detail in *Drug Facts and Comparisons* (loose leaf drug information service), Wolters Kluer Company, St. Louis, Mo., ©1997, pps. 3–17 and 54–57. Suitable herbals include, but are not limited to, wormwood (*artemisia absinthium*), mugwort (*artemisiae herba*), aniseed (*anisi fructus*), peppermint (*menthae pipertiae folium*), rosehips (*rosae pseudofructus*), and mixtures thereof. Herbals are described in more detail in *Herbal Drugs and Phytopharmaceuticals; A Handbook for Practice on a Scientific Basis*, CRC Press, Stuttgart, Germany, 1994. Vitamins and minerals may be present at levels up to and including the recommended daily allowances for healthy adults, including those levels recommended for pregnant and lactating women, or at the levels generally administered for dietary supplements. Herbals, and oral and enteral nutritional supplements may be included in the formulations of the present formulation from about 0% to about 20%.

Because the gel-forming polysaccharide has a tacky, self-adherent nature, it is not necessary to add a binder to the compositions of the present invention to achieve the desired tablet properties. However, a binder may optionally be added. The binder is generally present from about 0.01% to about 5%. Suitable binders include, but are not limited to: starches; gelatin; microcrystalline cellulose; polyvinyl pyrrolidone; cellulosics such as methyl cellulose, hydroxypropyl cellulose, hydroxypropylmethylcellulose, ethyl cellulose, and hydroxyethyl cellulose; other natural and synthetics gums such as carboxymethylcellulose, acacia, sodium alginate, and Veegum; and mixtures thereof. In one embodiment the binder has a glass transition temperature of less than about 125° C., in another embodiment, the glass transition temperature is less than about 110° C.

The present compositions may further comprise one or more sweeteners which may be additional to the fast dissolving and slow dissolving excipients. Suitable sweeteners include natural and artificial, water soluble, water insoluble and intense sweeteners. The sweetening agent may be dextrose, sucrose, maltose, dextrin, dried invert sugar, mannose, xylose, ribose, glucose, fructose, levulose, galactose, corn syrup, high fructose corn syrup, corn syrup solids, partially hydrolyzed starch, aspartame, saccharin, and hydrogenated starch hydrolysate or combinations thereof Natural or artificial intense sweeteners such as dipeptide based intense sweeteners, monellin, thaumaoccous danielli, and L-aspartyl L-phenylalanine methyl ester and soluble saccharin salts may also be incorporated as sweeteners. The amount of the sweetener will vary with the type of sweetener selected and the desired level of sweetness. Sweetening agents and flavoring agents are typically used in the present compositions at levels of from about 0.005% to about 5%, by weight of the composition. The additional sweeteners may be incorporated into one or more of the following: the tablet; the coating of the tablet; or the coating of the individual particles of gel-forming polysaccharide, where such coatings are employed.

Method of Making

The gel-forming polysaccharide in dry, powdered form may be dry blended with a fast dissolving excipient for a period of about 10 minutes. Where a slow dissolving excipient is included in the compositions of the present invention, it may be dry blended along with the gel-forming polysaccharide and the fast dissolving excipient. Generally, optional ingredients, where included, may be blended separately. The polysaccharide mixture and the optional ingredients may then be blended together for a period of about 5 minutes using any method known in the art. To avoid color separation in the final product, the colorant may be mixed with the gel-forming polysaccharide prior to mixing of the polysaccharide with any other ingredients.

Compositions of the present invention may be tabletted in any manner known in the art, such as wet granulation, fluidized bed agglomeration, wet granulation, direct compression or the like. Unlike psyllium, the gel-forming polysaccharide fraction of psyllium used herein is compressible. Therefore, direct compression, not previously appropriate for psyllium containing compositions is the preferred method for tabletting compositions of the present invention because of its ease and simplicity. Thus, if desired, the mixture is suitable for direct compression into tablets using pressures of from about 2000 to about 4000 psi.

Targeting the same average particle size for all formulation ingredients is effective for producing a formulation that mixes well and resists separation when the formulation flows. Larger particle sizes, at least 250 microns on average, of all ingredients are preferred to produce a chewable tablet with acceptable mouthfeel.

Method of Use

The compositions of the present invention are useful for the treatment of gastrointestinal disorders. These formulations can be used alone or in combination with other active substances for the treatment of constipation and laxation and for normalizing bowel function. The compositions of the present invention may also be effective for providing more complete evacuation of the bowel and thereby rendering a detoxifying effect. In addition, the compositions are useful for reducing human serum cholesterol and controlling blood glucose levels in diabetics and may be used alone or in conjunction with other actives substances.

The compositions of the present invention may be prepared in any solid dosage form known in the art. Alternatively, compositions may be utilized in powdered form and incorporated into various food products. In one embodiment the compositions may be tabletted for use as a swallowable or chewable tablet. In one embodiment, the compositions of the present invention are directly compressed into solid oral dosage forms suitable for chewing, such as chewable tablets, for consumption by the consumer. Each tablet may comprise from about 100 mg to about 5000 mg of gel-forming polysaccharide, in one embodiment a chewable tablet may comprise from about 1000 mg to about 1500 mg of gel-forming polysaccharide. The gel-forming polysaccharide should be administered at a level of at least about 2 grams, from about 1 to about 3 times per day.

It should be understood that the present invention relates not only to compositions suitable for treatment of humans, but also is suitable for the treatment an animal, e.g. household pets or other domestic animals, or animals kept in captivity.

EXAMPLES

Example A

Fractionation of Psyllium Seed Husk

Raw, unmilled psyllium seed husk (2 grams) is stirred with 0.2N sodium hydroxide (400 milliliters) containing sodium borohydride (400 milligrams) in a nitrogen atmosphere at ambient temperature for 90 minutes. The pH of the solution is from 10 to 11. The solution is passed through a pasteurizer at a temperature of 100° C. for a period of 50 seconds. Once pasteurized, the mixture is centrifuged for 20 minutes at 23,500×g. The supernatant is decanted from an insoluble fraction that settles out in the centrifuge bottle. The insoluble fraction is mixed with fresh sodium hydroxide/sodium borohydride solution (100 milliliters) and recentrifuged for 15 minutes to increase yield of the soluble fraction. The pH of the supernatant is adjusted to 5.5 by the addition of acetic acid at ambient temperature with stirring, forming a gel. The gel is desiccated with isopropanol added with high shear mixing. The isopropanol solution is then decanted from the gel. The solids content of the gel is 30%. The gel material is passed through an extruder and extruded into individual particles with an average particle size of 500 microns. The extruded particles enter a fluidized bed dryer fitted with a cyclonic airflow screen, such as a Conidur screen. The air temperature is maintained at 80° C. The gel temperature remains below 70° C. throughout the drying process. The particles are dried to a powder, with 90% of the water being removed. The yield of the gel-forming polysaccharide is 85%.

The following are representative oral compositions according to the invention.

Example 1

Chewable tablets, total weight 2.5 grams, are manufactured in the following manner: Where optional ingredients are desired, a pre-mix is prepared comprising a flavorant, a colorant and citric acid. The fluidized bed dried gel-forming polysaccharide, prepared in the manner described in Example A, is dry blended with sorbitol for 10 minutes, each component having an average particle size of about 500 microns. The pre-mix, if desired, is added and the mixture is blended for an additional 10 minutes. Magnesium stearate is added and the composition is blended for another 5 minutes. The mixture is directly compressed into tablets using pressures of from 2000 psi to 4000 psi. The final compositions comprise the following components by weight:

| Component | Example 1A | Example 1B | Example 1C | Example 1D |
|---|---|---|---|---|
| Gel-Forming Polysaccharide | 50.0% | 50.0% | 50.0% | 50.0% |
| Sorbitol (Neosorb P20/60) | 48.16% | 47.95% | 47.75% | 50.0% |
| Magnesium Stearate | 0.5% | 0.25% | 0.4% | |
| Flavorant | 0.4% | 0.6% | 0.6% | |
| Colorant | 0.14% | 0.2% | | |
| Citric Acid | 0.8% | 1% | 1.25% | |

Example 2

In another example, the mouthfeel of the final chewable tablets is modified by varying the ratio of gel-forming polysaccharide to fast dissolving excipient. The resulting chewable tablets are perceived as less drying, and leave little residue from the gel-forming polysaccharide in the mouth upon ingestion. The tablet is prepared in the same manner as the tablet of Example 1. The final tablets comprise the following components by weight:

| Component | Example 2A | Example 2B |
|---|---|---|
| Gel-Forming Polysaccharide | 40% | 35% |
| Sorbitol (Neosorb P20/60) | 58.16% | 62.8% |
| Magnesium Stearate | 0.5% | 0.4% |
| Flavorant | 0.4% | 0.6% |
| Colorant | 0.14% | 0.2% |
| Citric Acid | 0.8% | 1% |

Example 3

As a variation to Example 1 and 2, Mannitol, a slower dissolving excipient is added at low levels to the gel-forming polysaccharide mixture, with the Sorbitol. This approach modifies the in-use characteristics of the chewable tablets, providing a more luxurious, creamy mouthfeel. The final tablets comprise the following components by weight:

| Component | Example 3A | Example 3B | Example 3C |
|---|---|---|---|
| Gel-Forming Polysaccharide | 50% | 50% | 40% |
| Sorbitol (Neosorb P20/60) | 33.16% | 43.16% | 43.16% |
| Mannitol | 15% | 5% | 15% |
| Magnesium Stearate | 0.5% | 0.5% | 0.5% |

-continued

| Component | Example 3A | Example 3B | Example 3C |
|---|---|---|---|
| Flavorant | 0.4% | 0.4% | 0.4% |
| Colorant | 0.14% | 0.14% | 0.14% |
| Citric Acid | 0.8% | 0.8% | 0.8% |

Example 4

In Examples 1–3, the gel-forming polysaccharide fractions are comprised of discrete particles. These individual particles may be coated in any manner known in the art, such as fluidized bed agglomeration or the like. Slowing the rate of hydration of the gel-forming polysaccharide in the mouth may be accomplished through coating the gel-forming polysaccharide, thereby improving mouthfeel. The coating employed will act as a barrier to slow down water absorption. Simple mixing of the following components will render an acceptable coating formulation:

| Coating formulation: | |
|---|---|
| Isopropanol | 94.5% |
| Eudragit RD100 | 5% |
| Polyethylene Glycol | 0.5% |

The coated gel-forming polysaccharide particles are dried and combined with the excipients as described in Examples 1–3.

Example 6

Alternatively, the coating can be applied directly to a chewable tablet containing the gel-forming polysaccharide. Additionally, it may be desired to include a flavorant within the coating composition. The coating may be applied in any manner known in the art.

| Coating formulation: | |
|---|---|
| Ethanol | 94% |
| Polyethylene Glycol | 5% |
| Flavorant | 1% |

Example 7

It may be desirable to granulate the gel-forming polysaccharide with excipients and then compress the composition into a solid dosage form. Granulation may be achieved using demineralised water, which can then be removed by fluidized bed drying. It is not necessary to add a binder to these compositions.

| Granule formulation without an additional binder: | |
|---|---|
| Gel-Forming Polysaccharide | 60% |
| Maltitol | 38.05% |
| Flavorant | 0.6% |
| Colorant | 0.3% |
| Citric Acid | 1.0% |

The components may be mixed in the same manner as in Example 1. Granules thus produced are mixed with magnesium stearate (0.5%) and the resulting mixture can be compressed into a solid oral dosage form.

| Granule formulation with an additional binder: | |
|---|---|
| Gel-Forming Polysaccharide | 60% |
| Maltitol | 28.05% |
| Avicel | 10% |
| Flavorant | 0.6% |
| Colorant | 0.3% |
| Citric Acid | 1.0% |

The components may be mixed in the same manner as in Example 1. Granules thus produced are mixed with magnesium stearate (0.5%) and the resulting mixture can be compressed into a solid oral dosage form.

Example 8

Chewable tablet, comprising a combination of the fluidized bed dried gel-forming polysaccharide (prepared as in Example 1) and vitamin and mineral components are prepared by pre-mixing the vitamin and mineral components with standard mixing. A second pre-mix is prepared by combining a flavorant, corlorant and citric acid. The gel-forming polysaccharide is combined with Sorbitol and the mixture was dry blended for 10 minutes. The vitamin and mineral pre-mix is added and the resulting mixture is dry blended for an additional 10 minutes. The second pre-mix is subsequently added and dry blending continued for 10 minutes. Magnesium stearate is added and the mixture is blended for 5 minutes. The mixture is directly compressed into tablet form using pressures from 2000 psi to 4000 psi. The resulting tablets comprise the following components:

| Component | Children's chewable Amount by Weight | Adult Chewable Amount by Weight |
|---|---|---|
| Gel-Forming Polysaccharide | 1.25 g | 1.25 g |
| Sorbitol (Neosorb P20/60) | 0.9904 g | 1.1 g |
| Magnesium Stearate | 20 mg | 20 mg |
| Flavorant | 15 mg | 15 mg |
| Colorant | 5 mg | 5 mg |
| Citric Acid | 20 mg | 20 mg |
| Vitamin A | 400 µg | 900 µg |
| Vitamin B-6 | 0.6 mg | 1.7 mg |
| Vitamin B-12 | 1.2 µg | 1.4 µg |
| Vitamin C | 25 mg | 90 mg |
| Vitamin D | 5 µg | 15 µg |
| Vitamin E | 7 mg | 15 mg |
| Vitamin K | 55 µg | 120 µg |
| Biotin | 12 µg | 30 µg |
| Choline | 250 mg | 250 mg |
| Folic Acid | 200 µg | 400 µg |
| Niacin | 8 mg | 16 mg |
| Pantothenic Acid | 3 mg | 5 mg |
| Riboflavin | 0.6 mg | 1.3 mg |
| Thiamin | 0.6 mg | 1.2 mg |
| Calcium | 200 mg | 300 mg |
| Chromium | 15 µg | 30 µg |
| Copper | 440 µg | 900 µg |
| Fluorine | 1 mg | 3 mg |
| Iodine | 90 µg | 150 µg |
| Iron | 10 mg | 8 mg |
| Magnesium | 100 mg | 150 mg |
| Manganese | 1.5 mg | 2.3 mg |
| Molybdenum | 22 µg | 45 µg |

-continued

| Component | Children's chewable Amount by Weight | Adult Chewable Amount by Weight |
|---|---|---|
| Phosphorous | 100 mg | 150 mg |
| Selenium | 30 μg | 55 μg |
| Zinc | 5 mg | 11 mg |

It is understood that the examples and embodiments described herein are for illustrative purposes only and that various modifications or changes in light thereof will be suggested to one of skill in the art without departing from the scope of the present invention.

What is claimed is:

1. A chewable tablet comprising:
   a) from about 10% to about 90% of a gel-forming polysaccharide derived from psyllium seed husk, said gel-forming polysaccharide comprising xylose and arabinose, wherein the xylose to arabinose dry weight ratio is at least about 3:1; and
   b) from about 10% to about 90% of a fast dissolving excipient selected from the group consisting of sorbitol, isomalt and mixtures thereof, wherein the chewable tablet further comprises a coating.

2. The oral composition of claim 1 wherein the gel-forming polysaccharide further comprises 1% to 2% of galactose.

3. The oral composition of claim 2 wherein the gel-forming polysaccharide comprises from about 55% to about 70% xylose.

4. The oral composition of claim 3 wherein the gel-forming polysaccharide comprises from about 15% to about 20% arabinose.

5. The oral composition of claim 4 wherein the xylose to arabinose ratio in the gel-forming polysaccharide is from about 3.3:1 to about 3.6:1.

6. The oral composition of claim 1 wherein the gel-forming polysaccharide is present at a level of about 25% to about 75%.

7. The oral composition of claim 6 wherein the gel-forming polysaccharide is present at a level of about 40% to about 60%.

8. The oral composition of claim 1 wherein the fast dissolving excipient dissolves in saliva in about 200 seconds or less.

9. The oral composition of claim 1 wherein the fast dissolving excipient is sorbitol.

10. The oral composition of claim 1 wherein the fast dissolving excipient is present at a level of about 25% to about 75%.

11. The oral composition of claim 10 wherein the fast dissolving excipient is present at a level of about 40% to about 60%.

12. The oral composition of claim 1 wherein the average particle size of the gel-forming polysaccharide is greater than about 250 microns.

13. The oral composition of claim 12 wherein the average particle size of the gel-forming polysaccharide is from about 250 to about 1000 microns.

14. The oral composition of claim 13 wherein the average particle size of the gel-forming polysaccharide is from about 350 to about 750 microns.

15. The oral composition of claim 1 wherein the average particle size of the fast dissolving excipient is from about 250 to about 1000 microns.

16. The oral composition of claim 1 further comprising from about 0.01% to about 30% of a slow dissolving excipient.

17. The oral composition of claim 16 wherein the slow dissolving excipient dissolves in saliva in more than 200 seconds.

18. The oral composition of claim 17 wherein the slow dissolving excipient is a slow dissolving sugar alcohol selected from the group consisting of mannitol, maltitol, maltodextrin, xylitol, and mixtures thereof.

19. The oral composition of claim 18 wherein the slow dissolving excipient is mannitol.

20. The oral composition of claim 1 further comprising at least one component selected from the group consisting of, lubricants, flavorants, colorants, binders, vitamins, minerals, oral nutritional supplements, enteral nutritional supplements, herbals and mixtures thereof.

21. The oral composition of claim 1 wherein the level of gel-forming polysaccharide in the chewable tablet is from about 100 mg to about 5000 mg.

22. The oral composition of claim 21 wherein the level of gel-forming polysaccharide in the chewable tablet is from about 1000 mg to about 1500 mg.

23. The oral composition of claim 1 wherein the coating material is selected from the group consisting of carnuba wax, polyethylene glycol, hydroxypropyl methylcellulose, copolymers of poly(acrylate, methacrylate), ethylcellulose, water soluble polymers derived from Indian corn and mixtures thereof.

24. The oral composition of claim 1 wherein the coating material is selected from the group consisting of carnuba wax, polyethylene glycol, hydroxypropyl methylcellulose, copolymers of poly(acrylate, methacrylate), ethylcellulose, water soluble polymers derived from Indian corn and mixtures thereof.

25. A chewable tablet comprising:
   a) from about 40% to about 60% of a gel-forming polysaccharide particulate derived from psyllium seed husk, said gel-forming polysaccharide comprising xylose and arabinose, wherein the xylose to arabinose dry weight ratio is at least about 3:1;
   b) from about 40% to about 60% of sorbitol; and
   c) from about 0.01% to about 30% of mannitol, wherein the chewable tablet further compromises a coating.

26. A chewable tablet with reduced allergenicity as compared to psyllium seed husk comprising:
   a) from about 10% to about 90% of a gel-forming polysaccharide particulate derived from psyllium seed husk, said gel-forming polysaccharide comprising xylose and arabinose, wherein the xylose to arabinose dry weight ratio is at least about 3:1; and
   b) from about 10% to about 90% of a fast dissolving excipient selected from the group consisting of sorbitol, isomalt and mixtures thereof, wherein the chewable tablet further comprises a coating.

27. The oral composition of claim 26 wherein the gel-forming polysaccharide has a level of allergenic protein that is less than about 10% of that present in psyllium seed husk.

28. The oral composition of claim 27 wherein the gel-forming polysaccharide has a level of allergenic protein that is less than about 5% of that present in psyllium seed husk.

29. A chewable tablet comprising:
   a) a gel-forming polysaccharide particulate derived from psyllium seed husk, said gel-forming polysaccharide comprising xylose and arabinose, wherein the xylose to arabinose dry weight ratio is at least about 3:1; and b) a fast dissolving excipient selected from the group consisting of sorbitol, isomalt and mixtures thereof, wherein the chewable tablet is essentially free of a binder, and wherein the chewable tablet further comprises a coating.

30. A method of provide an oral composition with reduced allergenicity as compared to psyllium seed husk administering a chewable tablet composition comprising:
   a) xylose and arabinose, wherein the xylose to arabinose dry weight ratio is at least about 3:1; and
   b) a fast dissolving excipient selected from the group consisting of sorbitol, isomalt and mixtures thereof.

31. The method of claim 30 wherein the gel-forming polysaccharide has a level of allergenic protein that is less than about 10% of that present in psyllium seed husk.

32. The method of claim 31 wherein the gel-forming polysaccharide has a level of allergenic protein that is less than about 5% of that present in psyllium seed husk.

33. The method of claim 30 wherein the gel-forming polysaccharide further comprises 1% to 2% of galactose.

34. The method of claim 33 wherein the gel-forming polysaccharide comprises from about 55% to about 70% xylose.

35. The method of claim 34 wherein the gel-forming polysaccharide comprises from about 15% to about 20% arabinose.

36. The oral composition of claim 35 wherein the xylose to arabinose ratio in the gel-forming polysaccharide is from about 3.3:1 to about 3.6:1.

37. The method of claim 30 wherein the oral composition further comprises a slow dissolving excipient.

* * * * *